United States Patent [19]

Barnes, Jr. et al.

[11] Patent Number: 4,645,602
[45] Date of Patent: Feb. 24, 1987

[54] PROCESS FOR PRODUCING REINFORCED MICROPOROUS MEMBRANE

[76] Inventors: Robert G. Barnes, Jr., 631 Brownstone Ridge, Meriden; Mark T. Meyering, 144 Powder Hill Rd., Middlefield, both of Conn. 06450

[21] Appl. No.: 651,376

[22] Filed: Sep. 17, 1984

Related U.S. Application Data

[63] Continuation of Ser. No. 332,068, Dec. 18, 1981, abandoned.

[51] Int. Cl.$^4$ .............................................. B01D 13/00
[52] U.S. Cl. .............................. 210/490; 210/500.38; 427/245
[58] Field of Search ............... 210/490, 489, 491, 346, 210/500.2, 500.38; 427/244, 245, 246; 264/41, 175, 45.1

[56] References Cited

U.S. PATENT DOCUMENTS

| | | | |
|---|---|---|---|
| 2,806,256 | 9/1960 | Smith-Johannsen | 264/49 |
| 2,940,871 | 6/1960 | Smith-Johannsen | 264/49 |
| 2,960,462 | 11/1960 | Lee et al. | 264/41 |
| 3,190,765 | 7/1965 | Yuan | 264/49 |
| 3,200,721 | 9/1965 | Holden | 264/49 |
| 3,208,875 | 9/1965 | Holden | 264/49 |
| 3,389,045 | 6/1968 | Jones et al. | 210/500.2 |
| 3,401,798 | 9/1968 | Nyrop | 210/346 X |
| 3,551,244 | 12/1970 | Forester | 210/490 |
| 3,556,305 | 1/1971 | Shorr | 210/490 |
| 3,615,024 | 11/1971 | Michaels | 210/500.2 X |
| 3,642,668 | 3/1972 | Bailey et al. | 264/49 X |
| 3,676,335 | 7/1972 | Lacey et al. | 210/653 X |
| 3,679,540 | 7/1972 | Zimmerman et al. | 264/41 |
| 3,709,841 | 1/1973 | Quentin | 264/41 |
| 3,721,596 | 3/1973 | Drake | 264/49 |
| 3,744,642 | 7/1973 | Scala et al. | 264/41 |
| 3,762,566 | 9/1973 | Del Price | 210/490 |
| 3,876,738 | 4/1975 | Marinaccio et al. | 264/49 X |
| 3,894,166 | 7/1975 | Brown et al. | 210/500.2 X |
| 3,912,834 | 10/1975 | Imai et al. | 210/490 |
| 3,928,517 | 12/1975 | Knight et al. | 264/41 |
| 3,951,815 | 4/1976 | Wrasidlo | 210/490 |
| 4,005,012 | 5/1977 | Wrasidlo | 210/490 |
| 4,026,977 | 5/1977 | Bourganel | 264/41 |
| 4,061,821 | 12/1977 | Hayano et al. | 264/41 |
| 4,201,838 | 5/1980 | Goldberg | 210/446 X |
| 4,203,847 | 5/1980 | Grandine, II | 210/490 |
| 4,203,848 | 5/1980 | Grandine, II | 210/490 |
| 4,207,182 | 6/1980 | Marze | 210/23 F |
| 4,214,994 | 7/1980 | Kitano | 210/490 |
| 4,244,817 | 1/1981 | Vaganuma | 264/41 |
| 4,247,498 | 1/1981 | Castro | . |
| 4,276,172 | 6/1981 | Henne et al. | 210/490 |
| 4,277,344 | 7/1981 | Cadotte | 210/490 |
| 4,340,479 | 7/1982 | Pall | 210/490 |

FOREIGN PATENT DOCUMENTS 0005536 12/1979 European Pat. Off. .

Primary Examiner—Frank Spear
Attorney, Agent, or Firm—Michael E. Zall

[57] ABSTRACT

A process for producing an integral single layer polymeric microporous filter membrane within which a reinforcing web is embedded. The process comprises passing a reinforcing web through a first reservoir of casting solution of polymer and then simultaneously calendering both sides of the coated web to provide for penetration of the solution into the web and to remove substantially all entrapped air from the web. The calendered reinforcing web is then passed through a second reservoir of casting solution and then through a quenching bath to form micropores throughout the coatings.

7 Claims, 1 Drawing Figure

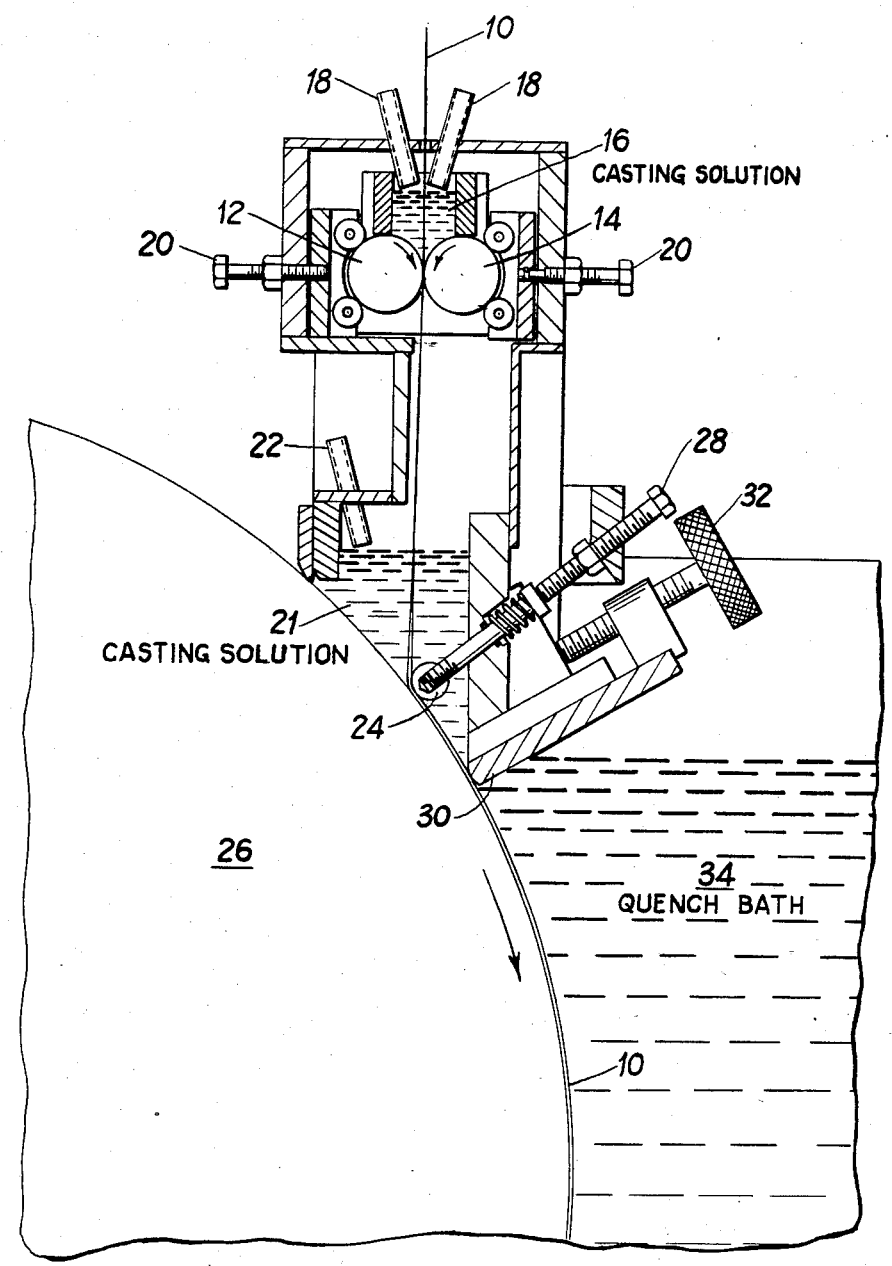

PROCESS FOR PRODUCING REINFORCED MICROPOROUS MEMBRANE

This is a continuation of co-pending application Ser. No. 332,068 filed on Dec. 18, 1981, now abandoned.

BACKGROUND OF THE INVENTION

1. Field of the Invention

This invention relates to microporous membranes, and more particularly to reinforced microporous membranes suitable for the filtration of aqueous fluids, such as biological liquids and high purity water used in the electronics industry.

2. Prior Art

Nylon microporus membranes are well known in the art. For example, U.S. Pat. No. 3,876,738 to Marinaccio et al (1975) describes a process for preparing nylon microporous membranes by quenching a solution of a film forming polymer in a non-solvent system for the polymer. European Patent Application No. 0 005 536 to Pall et al (1979) describes a similar type nylon membrane and process.

Other type polymeric microporous membranes, including nylon, and processes for producing such membranes are described, for example, in the following U.S. Pat. Nos.

3,642,668 to Bailey et al (1972);
4,203,847 to Grandine, II (1980);
4,203,848 to Grandine, II (1980); and
4,247,498 to Castro (1980).

Commercially available nylon microporous membranes are available from Pall Corp., Glencove, N.Y., under the trademark ULTIPOR N66. Another commercially significant membrane made of polyvinylidene fluoride is available from Millipore Corp., Bedford, Mass., under the trademark DURAPORE. This membrane is probably produced by the aforementioned Grandine, II patents.

Additionally, the Assignee of this application is selling two types of cationically charge modified nylon microporous membranes under the trademark ZETA-POR. These membranes are described and claimed in U.S. Ser. No. 268,543 filed on May 29, 1981 to Barnes et al, now U.S. Pat. No. 4,473,475, and U.S. Ser. No. 314,307 filed on Oct. 23, 1981 to Ostreicher et al, now U.S. Pat. No. 4,473,474. Barnes et al describes the use of charge modified membranes for the filtration of high purity water (18 megohm-centimeter resistivity) used in the electronics industry; and Ostreicher et al describes the use of charge modified membranes for the filtration of parenteral or body liquids.

Generally, the methods for producing a microporous membrane include spreading a casting solution on a substrate to form a thin film thereon, which eventually is formed into a microporous membrane. For example, the aforementioned Marinaccio et al process produces a microporous membrane through the quench technique. This technique involves casting or extruding a solution of a film-forming polymer in a solvent system, casting the solution on a substrate to form a film and quenching the film in a bath which includes a non-solvent for the polymer. The Pall application involves a similar type process.

The aforementioned Pall application is the most relevant known prior art relating to the formation of microporous membranes into useful laminates for filtration discs, cartridges, etc. As described by Pall a polymer solution is cast on a substrate which may be porous or non-porous to form a thin microporous membrane on the substrate. The membrane produced may then be removed from the substrate, washed and combined, i.e. laminated, with another similar type membrane to form a dual layer membrane. This dual layer membrane is then dried under restraint forming a membrane having particle removal characteristics superior to those of the individual layers. Pall indicates that the membrane layers can have the same or different porosities, have tapered pores or uniform pores, and be supported or unsupported. If a membrane layer is supported the substrate upon which it is cast is not removed from the membrane, i.e. the substrate is an integral part of the membrane. Such a substrate is preferably a porous material that is wetted by the polymer solution so that the solution will penetrate the substrate during casting and become firmly attached thereto during formation of the microporous membrane. Pall states that such supported membranes have a somewhat higher pressure drop than unsupported membranes (i.e. lower flow rate for a given pressure differential), and that the increase in pressure drop is small if the supporting web has an open structure.

The problems associated with the dual layer type filtration membranes of Pall, are comparatively major when one considers the uses for such membranes (e.g. the filtration of parenteral or body liquids, high purity water, pharmaceuticals, beverages, etc.), the small pore size of the membranes (i.e., less than about 1.2 microns and usually about 0.2 microns), the manipulation required to form the membrane into usable forms, e.g. cartridges, and that preferably the membrane be useful with either side facing upstream. It has been found by the Assignee in the production of the commercial forms of the membranes described in the aforementioned Barnes et al and Ostreicher et al applications, that a non-reinforced dual layer membrane is generally too fragile, e.g. tends to crack when pleated to form filtration cartridges and generally causes too high a reject rate for cartridges used as sterilizing filtration media. In attempting to solve this problem by reinforcing the membranes by casting directly onto a reinforcing web and then laminating the layers together, it was found that very careful control over the casting conditions had to be maintained to avoid streaking, non-uniform wetting of the web, pin-holes, air-bubbles, etc. More specifically, it was discovered that air bubbles tended to form in the membrane in the areas of crossover between the pieces of yarn forming the web, and that such air bubbles cause objectionable voids or pockets in the final membrane. In some instances, such air bubbles resulted in an opening through the membrane which rendered it useless. Additionally, as indicated in Pall, the pressure drop across the membrane tended to be too high (or the flow too low).

Additional prior art of interest, none of which solve all of the above problems, are the following U.S. Nos.:

2,806,256 and 2,940,871 to Smith-Johannsen (1960) describes producing a microporous film by fusing fine particles of thermoplastic material while dispersed throughout a viscous or continuous inert matrix medium and then dissolving out the inert matrix medium. The membrane may be used for filtration. The thermoplastic material may be a polyamide. The dispersion may be calendered, knifed, molded, dip coated, or rolled onto a backing material to reinforce the film. The backing material is desirably at least as porous as the microporous film itself.

2,960,462 to Lee et al (1960) describes the use of laminated permeation membranes for the separation of organic chemical mixtures. The laminated membrane consists of a thin layer or film of a selective membrane material and a thicker film of a membrane material having a higher permeation rate. The laminated membrane is employed so that the film layer having the higher permeation rate is in contact with the mixture of the chemicals to be separated.

3,190,765 to Yuan (1965) describes, polymeric films adherently united to fibrous substrates. The primary use is as a substitute leather, although the materials may be used as filters. The products are produced by applying a layer of a polymer-containing solution to one or both sides of a flexible porous fibrous substrate. The leather when bathed and dried in the manner described therein, becomes a microporous polymeric layer integrally united to the fibrous substrate. The sheet material formed has a high permeability to vapors and relatively low permeability to liquids, i.e., it is breatheable yet water repellent.

3,100,721 and 3,208,875 to Holden (1965) describes the manufacture of leather like sheet materials having a microporous/durable elastomeric material in superposed adherence with a fabric or other porous fibrous sheet material. The uses for such vapor permeable sheets are as shoe uppers, upholstery and clothing. The sheet products are produced by applying a layer of a solution containing a polymer to one or both sides of a flexible porous fibrous substrate.

3,389,045 to Jones et al (1968) describes a method of producing thin thermoplastic films having a multicolored ombre. Such films are used for decorative curtains, wearing apparel, surface covering for floors, walls, furniture, etc. The process involves the controlled calendering of several separate thermoplastic materials of different colors.

3,551,244 to Forester et al (1970) describes an ultrathin polymer film on a support membrane for use as a reverse osmosis membrane.

3,556,305 to Shorr (1971) describes a reverse osmosis membrane comprising (a) an anisotropic membrane, (b) a very thin layer of a film forming adhesive polymer and (c) a very thin diffusive type membrane film overlying the adhesive polymer.

3,615,024 to Michaels (1971) describes an anisotropic polymeric membrane which is formed by casting the film on an impermeable surface, e.g., a glass or metal surface, or a permeable surface, e.g. paper. Particularly advantageous materials for use are permeable non-wettable, non-woven sheets, for example, polyolefin fiber felts.

3,679,540 to Zimmerman et al (1972) describes reinforced microporous films used for sterile packaging, hospital bed sheets, and pillow liners. The reinforced films are produced by laminating a specifically characterized microporous polymer film onto a specifically characterized microporous film. The reinforced film is said to have increased strength and high permeability.

3,709,841 to Quentin (1973) describes sulphonated polyarylether-sulphone ion exchange membrane combined with a reinforcing support.

3,721,596 to Drake (1973) describes an osmotic desalination membrane produced by immersing an apertured support in a casting solution and then allowing the film to set.

3,744,642 to Scala et al (1973) describes a desalination membrane having a membrane layer of polymeric material, e.g. polyamide, in contact with a substrate. The membranes produced on the substrate are generally homogenous and between 0.1 and 1.0 mils thick. The membrane can coat one or both sides of the substrate and can be applied continuously. The substrate can be interwoven or felted fibers of paper, plastic, glass, etc. The thin polymeric film which is formed comprises interlocked polymer chains in contact with each other and which generally extend into the pores within the substrate.

3,762,566 to Del Pice (1973) describes a supported semi-permeable membrane produced by impregnating the surface of a porous support with a non-solvent for the film forming polymer used in a subsequently applied casting solution.

3,912,834 to Imai et al (1975) describes a reinforced ultrafiltration or reverse osmosis membrane. Porous backing materials are impregnated prior to coating with a film-forming polymer solution, with a liquid in which the polymer is insoluble to the extent that at least one of the surfaces of the backing material has remained substantially free from the liquid while other portions, especially the interior thereof become wet. The coating solution of the film-forming polymer in a volatile solvent is then applied to the surface of the backing material and the coating layer is then gelled or otherwise treated to give a selectively permeable membrane on the backing material.

3,951,815 to Wrasidlo (1976) describes a composite semi-permeable membrane wherein an ultra thin film is formed in situ upon a microporous substrate. More specifically, a polysulfone membrane is cast on to a tightly woven dacron cloth. This fabric reinforced polysulfone substrate is then presoaked in a cyanoethylated polyethylenimine aqueous solution. The membrane is dried and disposed upon a glass plate and immersed again in the same aqueous solution to produce the composite "polyamide membrane."

4,005,012 to Wrasidlo (1977) describes a process for producing a semi-permeable anisotropic membrane useful in reverse osmosis processes. The membranes are prepared by forming a polymeric thin film possessing semi-permeable properties, on a microporous support.

4,026,977 to Bourganel (1977) describes a process for producing an anisotropic membrane by casting a solution of a sulfonated polyaryl ether/sulfone on a support immersing the support coated with the layer of polymer in a coagulating bath and then recovering the resulting membrane. The support can also be covered with a reinforcement material intended to reinforce the membrane. This reinforcement material can consist of a woven fabric, a net or knitted fabric.

4,061,821 to Hayano et al (1977) describes a semipermeable composite membrane consisting of a porous substance and a reinforcing material embedded therein. The method of producing the membrane comprises impregnating the reinforcing material with a coagulating liquid. The reinforcing cloth may be polyester. The semipermeable membrane may be copolymers of acrylonitrile, cellulose acetate, polyamides, polyurethanes, polysulfones.

4,201,838 to Goldberg (1980) describes a laminated microporous article consisting of at least two layers or plys of thermoset or thermoplastic microporous material and a polyester non-woven, heat bonded web. The laminate is particularly useful as a battery separator.

4,207,182 to Marze describes a screen supported or reinforced semi-permeable membrane which is embedded in a flexible support of woven fabric, non-woven fabric or a net. The membrane is produced by casting a solution of a polymer on the reinforcement material followed by removal of the solvent, e.g. by evaporation and/or coagulation.

4,214,994 to Kitano (1980) describes a reverse osmosis membrane for use to purify sea water into plain water. The membrane comprises a skin layer as an active layer and a gel layer to support the skin layer. An improvement of flux, i.e., passing rate of purified water, is achieved by burying a porous sheet, such as plain woven cloth or non-woven fabric, in the gel layer.

4,244,817 to Yaginuma (1981) describes a process for preparing a semi-permeable membrane comprising coating a thin polyamine film on a reinforced microporous substrate and then subsequently treating to crosslink the polyamine.

4,277,344 to Cadotte (1981) describes a process for making a reverse osmosis membrane by coating a porous support layer with a polyamine component and then contacting the thus coated support with the polyacyl halide component to initiate polymerization.

OBJECTS AND SUMMARY OF THE INVENTION

It is an object of this invention to provide a novel reinforced laminated filtration membrane and novel process for producing such membrane.

It is a further object of this invention to provide a reinforced laminated filtration membrane particularly suitable for the filtration of biological or parenteral liquids.

It is still a further object of this invention to provide a reinforced laminated filtration membrane particularly suitable for the filtration of high purity water for the electronics industry.

It is still another object of this invention to provide a reinforced laminated membrane which is characterized by unexpected high flow rates for a given pressure differential, a highly uniform surface, durability and flexibility.

These and other objects of this invention are attained by the novel reinforced laminated filtration membrane of this invention. The membrane comprises:

(a) a porous reinforcing web impregnated with a polymeric microporous inner membrane; and (b) at least one polymeric microporous outer membrane laminated to each side of the impregnated web, wherein the pore size of the inner membrane is greater than the pore size of the outer membranes.

The invention is further directed to a process for producing the reinforced membrane by impregnating the reinforcing web with the inner membrane, followed by laminating the outer membranes to each side of the impregnated web.

The preferred polymeric membranes are nylon having a pore size of from 0.05 to 1.2 microns.

The reinforced laminated filtration membrane of this invention is preferably cationically charge modified. The charge modified membrane is particularly useful for the filtration of parenteral or biological liquids and high purity water (at least about 18 megohm-centimeter resistivity) for the electronics industry.

BRIEF DESCRIPTION OF THE FIGURE

The FIGURE forming a part of this specification is a cross-sectional side elevation of a preferred apparatus used for impregnating the reinforcing web with microporous membrane by the preferred process of this invention.

DETAILED DESCRIPTION OF THE INVENTION

The inner and outer membranes of the reinforced laminated filtration membrane of this invention are produced from an organic polymeric microporous membrane. Such membranes are well known in the art.

By the use of the term "microporous membrane" as used herein, it is meant a porous single layer membrane having a pore size of at least 0.05 microns or larger or an initial Bubble Point (IBP), as that term is used herein, in water of less than 120 psi. A maximum pore size useful for this invention is about 1.2 microns or an IBP of greater than about 8 psi. Preferably, but not necessarily, this membrane is substantially symmetrical and isotropic. By "symmetrical" it is meant that the pore structure is substantially the same on both sides of the membrane. Asymmetric membranes, i.e. membranes having one side formed with a very tight thin layer which is supported by a much more porous open structure, may also be utilized in this invention. By the use of the term "isotropic" it is meant the membrane has a uniform pore structure throughout the membrane.

Preferably, the microporous membranes are hydrophilic. By the use of the term "hydrophilic" in describing the membranes, it is meant a membrane which adsorbs or absorbs water. Generally, such hydrophilicity is produced by a sufficient amount of hydroxyl (—OH—), carboxyl (—COOH), amino (—NH$_2$) and/or similar functional groups on the surface of the membrane. Such groups assist in the adsorption and/or absorption of the water onto the membrane. Such hydrophilicity is particularly useful in the filtration of aqueous fluids.

Preferred microporous membranes are those produced from nylon. The term "nylon" is intended to embrace film forming polyamide resins including copolymers and terpolymers which include the recurring amido grouping.

While, generally, the various nylon or polyamide resins are all copolymers of a diamine and a dicarboxylic acid, or homopolymers of a lactam and an amino acid, they vary widely in crystallinity or solid structure, melting point, and other physical properties. Preferred nylons for use in this invention are copolymers of hexamethylene diamine and adipic acid (nylon 66), copolymers of hexamethylene diamine and sebacic acid (nylon 610), and homopolymers of poly-o-caprolactam (nylon 6). Alternatively, these preferred polyamide resins have a ratio of methylene (CH$_2$) to amide (NHCO) groups within the range about 5:1 to about 8:1, most preferably about 5:1 to about 7:1. Nylon 6 and nylon 66 each have a ratio of 6:1, whereas nylon 610 has a ratio of 8:1. The nylon polymers are available in a wide variety of grades, which vary appreciably with respect to molecular weight, within the range from about 15,000 to about 42,000 (number average molecular weight) and in other characteristics.

The highly preferred species of the units composing the polymer chain is polyhexamethylene adipamide, i.e. nylon 66, and molecular weights above about 30,000 are preferred. Polymers free of additives are generally preferred, but the addition of antioxidants or similar additives may have benefit under some conditions.

Additionally, any of the hydrophilic or hydrophobic type microporous membranes used in commercially available membranes produced by numerous companies, are potentially suitable for forming into the reinforced laminated microporous filtration membranes of this invention, for example, Pall Corp.'s ULTIPOR N66 (nylon), Millipore's DURAPORE (polyvinylidene fluoride), Gelman Sciences Inc.'s METRICEL (esters of cellulose, PVC copolymer) TUFFRYN, TEFLON, VERSAPOR (acrylic copolymer), Ghia Corp's nylon and polypropylene membranes and cellulose acetate/nitrate membranes.

The preferred inner and outer microporous membranes are produced from nylon by the method disclosed in U.S. Pat. No. 3,876,738 to Marinaccio et al. Another method for producing such membranes is described in European Patent Application No. 0 005 536 to Pall. The entire disclosures of both of these references are incorporated herein by reference.

Both of these methods for producing nylon microporous membranes may be described as "quench techniques", i.e. casting or extruding a solution of a film forming polymer onto a substrate and quenching the cast film. In the production of the reinforced laminated membrane of this invention the inner microporous membrane is formed on a substrate which is the reinforcing web and the outer microporous membrane is formed on a substrate which is nonporous, i.e. a glass plate, stainless steel drum or belt.

Broadly, Marinaccio et al produces microporous membrane by casting or extruding onto a substrate a casting solution of a film-forming polymer in a solvent system and quenching in a bath comprised of a nonsolvent system for the polymer. The most important parameter responsible for developmemt of micropores in the film (e.g. pore size) according to Marinaccio et al, is the solvent system employed with the polymer and the nonsolvent system used in quenching the film. The selection of the solvent for the polymer is determined by the nature of the polymer material used and can be empirically determined on the basis of solubility parameters described in detail in Marinaccio et al.

The casting solution for forming the preferred nylon microporous membrane is a nylon polymer in a solvent system for the polymer. The solvent system comprises a mixture of at least one solvent and one nonsolvent for the polymer. The solvents which can be used with alcohol soluble nylons include solvents such as lower alkanols, e.g. methanol, ethanol and butanol, and mixtures thereof. It is known that nonalcohol soluble nylons will dissolve in solvents of acids, for example, formic acid, citric acid, acetic acid, maleic acid and similar acids. The nylon solutions after formation are diluted with a nonsolvent for the nylon which is miscible with the nylon solution. Dilution with non-solvent may, according to Marinaccio et al, be effected up to the point of incipient precipitation of the nylon. The nonsolvents are selected on the basis of the nylon solvent utilized. For example, when water miscible nylon solvents are employed, water can be the nonsolvent. Generally, the nonsolvent can be water; methyl formate; aqueous lower alcohols, such as methanol and ethanol; polyols such as glycerol, glycols, polyglycols, and ethers and esters thereof; and mixtures of the aforementioned.

The aforementioned Pall application describes another similar method which may be used for the conversion of nylon polymer into nylon microporous membrane. Broadly, Pall provides a process for preparing skinless hydrophilic alcohol-insoluble polyamide resin from a polyamide casting solution. The casting solution is formed by inducing nucleation of the solution by the controlled addition of a nonsolvent for the polyamide resin to obtain a visible precipitate of polyamide resin particles.

The casting solution, e.g. whether that of Marinaccio et al or Pall, is then spread on a substrate, i.e. reinforcing web or non-porous substrate, to form a thin film thereon. The cast film is then contacted with a quenching bath comprising a non-solvent system for the polymer for a time sufficient to form micropores in the film. The preferred quench bath for forming a nylon microporous membrane comprises a nonsolvent system of methanol and water or formic acid and water.

These preferred nylon membranes, i.e. described in Marinaccio et al and Pall, are characterized by an isotropic structure, having a high effective surface area and a fine internal microstructure of controlled pore dimensions with narrow pore size distribution and adequate pore volume. For example, a representative 0.22 micron rated nylon 66 membrane (polyhexamethylene adipamide) exhibits an Initial Bubble Point (IBP) of about 45 to 50 psid, a Foam All Over Point (FAOP) of about 50 to 55 psid, provides a flow of from 70 to 80 ml/min of water at 5 psid (47 mm. diameter discs), has a surface area (BET, nitrogen adsorption) of about 13 m 2/g and a thickness of about 4.5 to 4.75 mils.

The reinforced laminated filtration membrane of this invention has as an essential element thereof, a porous reinforcing web impregnated with a polymeric microporous inner membrane. Such an impregnated web is preferably produced, by casting a sufficient amount of the casting solution onto the porous reinforcing web to form a web having a coating solution thereon. The coated reinforced web is then contacted with the quenching bath.

The reinforcing web is a porous material which is preferably wettable by the casting solution to maximize impregnation of the casting solution during casting and become firmly attached to the web during precipitation of the polymeric membrane, e.g. nylon. It is not essential, however, that the web be wettable by the casting solution. If the web is not wettable, the casting solution coating will be largely confined to the surface of the web but is nonetheless adherant thereto due to impregnation of the solution into the web and adhesion of the membrane to the web.

Such wettable and nonwettable reinforcing webs can, for example, be made of nonwoven textiles and cloth, as well as netting of various types, including extruded plastic filament netting, papers and similar materials. Reinforcing webs which are non-wettable by the casting solution may be fine-pored non-woven webs made from fibers such as, polypropylene or polyethylene. Suitable wettable reinforcing webs include: polyesters, as nonwoven fibrous webs or woven webs, using monofilaments or multifilament yarn, the monofilaments being preferred in terms of open structure and lower pressure drops; polyamide fiber woven webs, woven and nonwoven webs of aromatic polyamides, and other relatively polar fibrous products such as cellulose, regenerated cellulose, cellulose esters, cellulose ethers, glass fiber, and similar materials. Cellulosic and synthetic fiber filter papers may also be used as the reinforcing web as well as perforated plastic sheets and open mesh expanded plastics. If the substrate is relatively coarse or in a very open weave structure, even if the fibers are not substantially wetted by the resin solution, the substrate may nonetheless be impregnated by the membrane material. Thus such non-wettable materials such as polypropylene and polyethylene can be impregnated by the membrane if they have a sufficiently open structure.

More specifically, a preferred reinforcing fiber is a polyester spun bonded non-woven web trademark REEMAY (Grade 2250) from Du Pont. Other specific reinforcing webs are polyester webs such as REEMAY Grades 2105 and 2111, Eaton Dikemann Corp's HOLLYTEX Grades 3251, 3252 and 3257; and polypropylene webs such as HOLLYTEX Grades 6001 and 6003, Kendall Corp's NOVONETTE Grade SP-160.15, Crown Zellerbach's 0.75 oz/sq. yd., Kendall's WEBRIL M1103, and Lutravil Sales Co.'s LUTRASIL 5015, 5020 and 5030.

A preferred manner of making the impregnated reinforcing web is by casting a sufficient amount of the casting solution onto the porous reinforcing web to form a web having a coating solution thereon. This coating solution is then calendered, i.e. pressed, preferably by rollers, into the web under conditions of temperature, pressure and time sufficient to reduce the viscosity of the coating solution sufficiently to ensure enhanced penetration of the coating solution into the web and to remove substantially all entrapped air therefrom to thus form a coated web. Such conditions of temperature, pressure and time are highly dependant on the type reinforcing web utilized, the casting solution, type rollers etc. Such conditions can be readily determined by one skilled in the art by noting the penetration of the solution into the web, and pin holes and bubbles in the final coating. The thus coated web is then subsequently treated by casting a sufficient amount of casting solution thereon to form a coated web having an additional coating solution thereon. This so coated web is then quenched in a quenching bath to form the impregnated web to which the outer membranes are then subsequently laminated.

A preferred apparatus for producing such an impregnated reinforcing web is shown in the FIGURE of this specification. In the apparatus depicted a reinforcing web (10) is fed by suitable means between calendering rollers (12 & 14). Surrounding the reinforcing web (10) above the calendering rollers (12 & 14) is first reservoir (16) containing casting solution which continuously contacts the reinforcing web (10) and is continuously calendered into the web by rollers (12 & 14). Feed pipes (18) feed casting solution into reservoir (16) to insure that the web (10) is surrounded with a sufficient quantity of casting solution. Adjusting screws (20) adjust the calendering pressure exerted by rollers (12 & 14) against web (10).

The thus coated web (10) then passes through a second reservoir (21) preferably containing the same casting solution as reservoir (16). Feed pipe (22) feeds casting solution into reservoir (21) to insure that the web (10) is surrounded with a sufficient quantity of casting solution. Guide bar (24) guides web (10) so that it conforms to the contour of casting drum (26). Guide bar (24) may be adjusted by adjusting screw (28). The casting solution coats web (10) which then passes under casting blade (30). The thickness of the coating on web (10) may be adjusted by moving casting blade (30) toward or away from casting drum (26) by calibrated push-pull screw (32). The so coated web then passes through reservoir (34) containing a quench bath which solidifies the polymer to form micropores in the coating to thus form the impregnated web.

The preferred manner of utilizing the aforementioned apparatus for producing the preferred impregnated reinforcing web is as follows:

Preliminary Setting of the Calendering Rollers (12 & 14)

The calendering rollers (12 & 14) are spaced to provide a slip fit for the reinforcing web (10). Thus, they are typically opened to an approximately ½ mil greater gap than the web thickness. The web (10) is passed through the rollers (12 & 14) to insure that no noticeable drag occurs at any point across the width of the rollers (12 & 14). It is desirable not to squeeze the web (10) with the rollers (12 & 14) at this point, since any non-synchronous speed variations between the driven calendering rollers (12 & 14) and the rotating casting drum (26) will cause the web (10) to either develop slack or excess tension between these two points. A slip fit between the rollers (12 & 14) insures that the drum (26) alone will control web speed. It is also desirable to space the rollers (12 & 14) at a minimum gap for such slip fit, in order to maximize the calendering action by the rollers to the casting solution and to insure that no excessive amount of casting solution is being carried from first reservoir (16) into second reservoir (21), resulting in an uncontrolled increase in the level in reservoir (21). Adjustment of the calendering roller gap is effected by the adjustment of the roller axle supports (not shown in FIGURE) and the adjusting screws (20).

Preliminary Setting of Guide Bar (24)

The guide bar (24) spacing above the casting drum (26) must be set evenly across the web (10). It is normally set with a bar (24) to drum (26) spacing equal to the nominal thickness of the web. At this setting, a slight amount of drag is noticed when the loose web material is pulled between the bar (24) and drum (26) with the drum (26) not rotating. It is desirable to keep this gap at a minimum, as experience with this system has shown that a small increase in the gap causes a large change in the drum side casting solution coating thickness on the web. Even at the minimum clearance setting, a continuous, discrete drum side coating of membrane is effected.

Preliminary Setting of the Casting Blade (30)

The casting blade (30) has its depth adjusted by calibrated push-pull screws (32). This blade (30) controls (a) the overall thickness of the impregnated reinforcing web, and (b) the thickness of the top (quench side) coating of the casting solution on the web. It is typically set with a blade (30) to drum (26) gap which is several mils thicker than the nominal web thickness to insure enough free space for the excess quench side and drum side casting solution to pass through. When in operation, the web (10) is typically bordered on both edges with an approximately 1" (2.54 cm) wide bead of membrane. The most accurate control of the thickness of the impregnated reinforcing web is achieved by monitoring the thickness of this bead for it is insensitive to fluctuations in web thickness. Bead thickness is controlled by screws (32) which adjusts the blade gap.

Start-up and Operation of the Web Impregnating Apparatus

The web impregnating apparatus is started and operated in the following manner. The lead edge of the roll of reinforcing web, with appropriate back tension applied, is fed in a straight vertical manner into the apparatus. The web passes between the calendering rollers (12 & 14) underneath the guide bar (24) and under the casting blade (30). The web is further fed around the drum (26) and out of the quench bath reservoir (34) through rinsing zones (not shown) to a roll take-up (not shown). The reservoir (34) is then filled with quench bath composition to a level about ½" (1.27 cm) under the casting blade (30), such that no quench bath fluid penetrates into reservoir (21). The casting drum (26) and calendering rollers (12 & 14) are then rotated to feed the web (10) through the apparatus to the take-up system after the rinse zones. Web tension exiting the quench zone reservoir (34) and running through the rinse zone to the take-up should be about 5 lbs across the width of the web. Once smooth and synchronous running is assured, casting solution is fed into the calendering roller reservoir (16). When reservoir (16) is filled, the same casting solution is then fed into second reservoir (21). A continuous impregnation and coating of the web is observed below the casting blade (30). At this time, the level of the quenching bath reservoir (34) is raised to a point approximately ½" above the level defined by the point of web (10) passing under the casting blade (30) bringing the system to the preferred "zero quench" condition. Without this "zero quench" condition ripple imperfections are noted to occur transversely across the web at regular intervals.

After about 180° of arc travel on the drum (26) the web (10) is allowed to peel off of the drum (26) and enter into the rinsing tank. During start-up operations the impregnated reinforcing web is checked for the following:

(I) Membrane bead thickness and uniformity.
(II) Binding and stalling of the web.
(III) Smoothness and continuity of the drum side coating.
(IV) Smoothness and continuity of the quench side coating.

I. With the preferred apparatus, shown in the FIGURE, wet nylon membrane bead thickness was found to relate to overall impregnated web dry sheet thickness. For example, the impregnated web produced in Example XX showed the following relationship:

| Wet Bead Thickness (mils) | Dry Impregnated Web Thickness (mils) |
| --- | --- |
| 4.5 | 4.07 |
| 5.7 | 4.47 |
| 6.8 | 4.70 |
| 8.0 | 5.15 |

Thus the dry impregnated web thickness may be monitored by measuring the wet bead thickness.

II. Binding and stalling of the web may occur at two places, these being the nip of the calendering rollers (12 & 14) and the nip of the guide bar (24) and drum (26). Such binding most often occurs at the guide bar and drum nip and will require an upwards adjustment of the guide bar (24) to increase the bar to drum gap.

III. Smoothness and continuity of the drum side coating indicates that an adequate amount of casting solution has been deposited on the drum side of the web, that the quench bath is diffusing through the whole structure to completely congeal the casting solution before its removal from the drum (26), and that the proper drum surface speed has been chosen for the particular casting solution, web and impregnated web thickness chosen. A common imperfection on the drum side coating is a roughness caused by unquenched pockets of casting solution being pulled off of the drum at the release point. These rough areas are fibrous, stringy elongations of casting solution which quench as it is pulled through the quenching medium. This condition may be eliminated by several adjustments, these include:

(a) decreasing the overall thickness of the web coating at the casting blade (30); and/or
(b) lowering the guide bar (24) closer to the drum (26) to decrease the drum side coating thickness; and/or
(c) decreasing the running speed of the casting, resulting in a longer casting drum residence time.

IV. Smoothness and continuity of the quench side coating indicates that an adequate amount of casting solution is well positioned between the drum surface and the quench bath, and that the guide bar to drum gap is not so great as to favor a heavy drum side coating to the exclusion of the quench side coating.

The latter condition is a commonly encountered problem for the guide bar (24) has proven to be very sensitive, i.e. and easily jarred from its preliminary setting. Should the gap become too great, a condition of quench side "terry clothing" becomes evident. This condition occurs because an excessive layer of casting solution is collected underneath the web on the drum side (usually caused by virtue of too large a gap between the guide bar and drum) which develops a high fluid pressure underneath the web at the web's point of contact with the casting blade (30). This pressure forces the web to form a nip at the blade (30) through which a quench side coating cannot pass. The pressure is then relieved after the web passes into the quench bath fluid, by flowing through the tightly drawn web from the high pressure drum side to the low pressure quench side. This pressure differential causes the casting solution to move in an uneven fashion through the web by virtue of the non-uniformity of the web's porosity. This creates hills and valleys of casting solution on the quench side of the web, resulting in a material with a surface texture much like terry cloth.

The "terry clothing" condition may be eliminated in two ways: (a) with heavy terry clothing it is necessary to decrease the gap between the guide bar and the drum; and (b) with light terry clothing, it is sometimes possible to simply increase the overall thickness of the coating at the casting blade (30). This relieves the pressure differential on the drum side of the coating. This method may be the only recourse against terry clothing when the guide bar gap is so tight as to border on binding and stalling the web at this nip.

The casting solution levels in the reservoirs (16 & 21) are independently controlled and require maintenance of constant levels. The second reservoir (21) is ideally at a constant level throughout operation. Provisions are made to insure an equal head of casting solution on the drum side and quench side of the web. Reservoir (16) has provisions for the same control, however, excellent results have been obtained using unequal levels of casting solution for the quench side and drum side of the web.

The foregoing procedure and apparatus for forming the impregnated web substantially eliminates air bubbles, insures complete and uniform impregnation of the web with casting solution and eliminates substantial deviations in impregnation of the web regardless of the degree to which the web can be wetted by the casting solution.

The formation of the outer microporous membranes can be accomplished by any of the recognized methods familiar to the art. The preferred method is casting on a non-porous substrate using a knife edge or doctor blade which controls the thickness of the cast film. In general, the films will be cast at thicknesses in the range of from about 1 mil to about 20 mils, preferably from about 1 to about 10 mils (wet thickness). After the polymer solution is cast and quenched, the outer membrane is removed from the quench bath and substrate upon which it was cast. After the impregnated web and outer microporous membranes have been formed they are then washed.

The washed outer membranes are then laminated to the washed impregnated web by methods well known in the art, preferably by passing the three layers juxtaposed upon each other through heated rollers to heat laminate and dry the outer membranes to the impregnated web. Preferably such drying is under restraint to prevent shrinkage. Drying of the membranes under restraint is described in the Assignee's copending U.S. Ser. No. 201,086 to Repetti filed Oct. 27, 1980 now Defensive Publication T 103,601. The entire disclosure of this application is incorporated herein by reference. Generally, any suitable restraining technique may be used while drying, such as winding the laminated membrane tightly about a drying surface, e.g. a drum. Biaxial control is preferred and tensioning the laminated membrane on a stretching frame is considered the most preferred. Preferably, the restraint imposed affects no reduction in dimensions. The final drying and curing temperature for the reinforced laminated filtration membrane should be sufficient to dry and cure the membranes. Preferably this temperature is from about 120° C. to 140° C. for minimization of drying times without embrittlement or other detrimental affects to the membranes. The total thickness of the reinforced laminated filtration membrane of this invention is preferably from about 3 mils to about 30 mils and most preferably about 5 to 15 mils thick (dry thickness).

A critical requirement of this invention is that the pore size of the inner membrane be greater than the pore size of the outer membranes. This relationship may be determined for the same type microporous membranes by insuring that the Initial Bubble Point (IBP) of the inner membrane is less than the IBP of the outer membranes. ASTM F316-70 describe the methods by which the IBP is determined and the calculation of pore size for a membrane. This ASTM procedure is incorporated herein by reference.

Such a relationship between the pore size of the inner and outer membranes increases the flow rate through the reinforced membrane (for a constant differential pressure) in an unexpected manner. Preferably, the ratio of the pore size of the inner membrane to the outer membranes is from about 1.5:1 to about 6:1 for maximization of flow rate and bonding between layers. Higher ratios can be used, however such ratios will have a minimal effect on flow rate. Under the same conditions, for the same type membranes this usually means that the ratio of the IBP of the inner membrane to IBP of the outer membranes is about 1:1.2 to 1:6. Typically, this means that the outer membranes have a pore size of about 0.2 microns to about 0.85 microns and the inner membrane from about 0.45 microns to about 2.0 microns. A preferred laminated membrane has outer membranes of about 0.20 microns and an inner membrane of about 0.65 microns. Another preferred laminated membrane has outer membranes of about 0.45 microns and an inner membrane of about 0.85 microns. Preferably, both outer membranes are of the same pore size although this is not necessary to achieve most of the benefits of this invention.

The reinforced laminated filtration membrane may be rolled and stored for use under ambient conditions. It will be understood that the reinforced membrane may be formed into any of the usual commercial forms, for example, discs or pleated cartridges.

For so-called sterile filtrations involving biological liquids, the reinforced laminated filtration membrane is sanitized or sterilized by autoclaving or hot water flushing. The reinforced membrane of this invention is resistant to this type treatment, and retains its integrity in use under such conditions.

The reinforced membrane additionally is easy to handle and readily formed into convoluted structures, e.g. pleated configuration. By reason of its retained flow characteristics it may be employed directly in existing installations, without pumping modifications.

After formation of the reinforced laminated filtration membrane of this invention it may be treated in accordance with U.S. Ser. No. 314,307 filed Oct. 23, 1981 (now U.S. Pat. No. 4,473,474) to Ostreicher et al to produce a cationically charge modified microporous membrane particularly suitable for the filtration of parenteral or biological liquids; or in accordance with U.S. Ser. No. 268,543 filed May 29, 1981 (now U.S. Pat. No. 4,473,475) to Barnes et al to produce another type cationically charge modified microporous membrane particularly suitable for the filtration of high purity water, i.e. at least 18 megohm-cm resistivity, required in the manufacture of electronic components. The entire disclosures of both of these applications are incorporated herein by reference.

The reinforced laminated filtration membrane of this invention is characterized by unexpectedly high flow rates for a given differential pressure and also characterized by, durability, strength, uniformity, lack of pinholes and bubble defects. The preferred membranes may be used with either side of the membrane facing upstream.

Having now generally described this invention, the invention will become better understood by reference to specific examples. These examples are included herein for the purposes of illustration only and are not intended to be limiting of the invention, unless so specified.

EXAMPLES

The following are the measurement and test procedures utilized in all the Examples.

Thickness

The dry membrane thickness was measured with a ½ inch (1.27 cm) diameter platen dial indicator thickness gauge. Gauge accuracy was ±0.00005 inches (±0.05 mils).

Initial Bubble Point (IBP) and Foam-All-Over Point (FAOP) Tests

A 47 mm diameter disc of the membrane sample is placed in a special test holder which seals the edge of the disc. Above the membrane and directly in contact with its upper face, is a perforated stainless steel support screen which prevents the membrane from deforming or rupturing when air pressure is applied to its bottom face. Above the membrane and support screen, the holder provides an inch deep cavity into which distilled water is introduced. A regulated air pressure is increased until a first stream of air bubbles is emitted by the water wetted membrane into the quiescent pool of water. The air pressure at which this first stream of air bubbles is emitted is called the Initial Bubble Point (IBP)—see ASTM F316-70.

Once the Initial Bubble Point pressure has been determined and recorded, the air pressure is further increased until the air flow thru the wetted membrane sample, as measured by a flow meter in the line between the regulator and the sample holder, reaches 100 cc/min. The air pressure at this flow rate, is called Foam-All-Over-Point (FAOP).

Flow Rate Test

A 47 mm diameter disc of the membrane sample is placed in a testing housing which allows pressurized water to flow thru the membrane. Prefiltered water is passed thru the membrane sample at a pressure differential of 5 psid. A graduated cylinder is used to measure the volume of water passed by the membrane sample in a one minute period.

EXAMPLE I

Preparation of Outer Microporous Membranes

A representative nylon 66 membrane having a nominal suface area of about 13 m²/g and a nominal pore size rating of 0.2 microns was prepared by the method of Marinaccio et al, U.S. Pat. No. 3,876,738, utilizing:

(1) a casting solution of approximately 16 percent by weight nylon 66 (Monsanto Vydyne 66B), and the proper mixture of solvent formic acid and non-solvent methanol (see Table I) to produce the desired minimum Initial Bubble Point of 42 psi, at the necessary dope mixing temperature, time, pressure, etc. (as required by the method of Marinaccio);

(2) a quench bath composition of 30% methanol, 2.0% formic acid and 68% water by weight (regenerated as required by the method of Knight et al, U.S. Pat. No. 3,928,517);

(3) a casting speed of 96 inches/min on a 30" diameter casting drum; and (4) a quench bath temperature of 23° C.

The membrane was produced by casting the casting solution onto the drum just under the surface of the quench bath approximately 4.5 mils thick as cast wet, to obtain a dry single layer of approximately 2.5 mils. thick. The membrane was allowed to separate from the drum at about 180° of arc from the point of application and was guided out of the quench bath and into a series of high purity water rinsing zones. The wet membrane was then slit from the cast 40" width down to two 15" widths, and taken up on separate hollow cores in lengths of 200 feet. These outer membrane layers may be stored wet in this fashion for several days before subsequent processing. The Membrane Characteristics for these layers are obtained after drying a double-layered sample of this membrane under restraint conditions as required by the method of Repetti, U.S. Ser. No. 201,086 filed Oct. 27, 1981.

TABLE I

| Casting Solution Composition | |
|---|---|
| Nylon | 16.06 wt. % |
| Formic Acid | 77.01 wt. % |
| Methanol | 6.93 wt. % |
| Casting Solution Mixing Conditions | |
| Temperature | 30° C. |
| Time | 5 hrs. |
| Pressure psig | 1.0 psig |

| Membrane Characteristics | | | |
|---|---|---|---|
| IBP (psi) | FAOP (psi) | THICKNESS (mils) | Q (cc/min.) |
| 42.3 | 51.5 | 5.38 | 81.3 |

EXAMPLE II

Preparation of Outer Microporous Membranes

A representative nylon 66 membrane having a nominal surface pore size rating of 0.45 microns was prepared by the same method described in Example I. Changes in the casting solution composition and mixing conditions are noted in the Table II.

TABLE II

| Casting Solution Composition | |
|---|---|
| Nylon | 16.15 wt. % |
| Formic Acid | 77.45 wt. % |
| Methanol | 6.40 wt. % |
| Casting Solution Mixing Conditions | |
| Temperature | 30° C. |
| Time | 5.0 |
| Pressure-psig | 1.0 psig |

| Membrane Characteristics | | | |
|---|---|---|---|
| IBP (psi) | FAOP (psi) | THICKNESS (mils) | Q (cc/min.) |
| 29.7 | 34 | 5.83 | 170 |

EXAMPLE III

Preparation of Outer Microporous Membranes

A representative nylon 66 membrane having a nominal pore size rating of 0.65 microns was prepared by the same method described in Example I, except that the membrane was produced at a casting surface speed of 30 inches/min. on a casting drum of 12.5 inch diameter. The wet thickness of a sheet was 5.5 mils. Changes in the casting solution composition and mixing conditions are noted in the Table III.

TABLE III

| Casting Solution Composition | |
|---|---|
| Nylon | 16.00 wt. % |
| Formic Acid | 78.04 wt. % |
| Methanol | 5.96 wt. % |
| Casting Solution Mixing Conditions | |
| Temperature | 30° C. |
| Time | 3 hrs. |
| Pressure-psig | 0.0 |

| Membrane Characteristics | | | |
|---|---|---|---|
| IBP (psi) | FAOP (psi) | THICKNESS (mils) | Q (cc/min.) |
| 16.0 | 19.5 | 3.90 | 620 |

EXAMPLE IV THROUGH IX

Preparation of Impregnated Web

EXAMPLE IV

A representative nylon 66 impregnated web with a microporous membrane having a nominal pore size rating of about 0.65 microns was produced with a reinforcing web of DuPont Corporation's REEMAY 2250 polyester spunbonded non-woven (nominal web thickness of 3.5 mils, sheet weight of 0.50 oz/sq. yd., fiber denier of 2.2 and Frazier air flow* of 1100) by the preferred methods and apparatus described herein. A casting solution was prepared in the same manner as described in Example III.

*Frazier Air Flow determined by ASTM D-737-75, incorporated herein be reference.

During the preparation of the impregnated web, the guide bar gap was slightly less than 3.0 mils, the membrane edge bead thickness was maintained at 5.5 mils and a casting rate of 30 inches per minute was used. Several 150 foot rolls of this material were collected. Performance data on a single layer of this material prepared under restrained drying conditions, i.e. see Repetti, is given in Table IV. Performance data of this casting solution cast as a nonreinforced membrane is also included as control data.

In a manner similar to Example IV other type impregnated webs were produced using the casting solution of Example III. Performance data is given in Table IV.

EXAMPLE V

Reinforcing web: Eaton Dikeman Corp.

Hollytex 3257

Type: Polyester spunbonded and calendered nonwoven
Nominal Web Thickness: 3.0 mils
Sheet weight: 1.00 oz/sq. yd.
Fiber denier: 2.2
Frazier Air Flow: 300
Membrane bead thickness: 5.0 mils
Surface Speed: 30 inches/min.

EXAMPLE VI

Reinforcing Web: Eaton Dikeman Corp.

Hollytex 3251

Type: Polyester spunbonded and calendered nonwoven
Nominal Web Thickness: 2.0 mils.
Sheet weight: 0.50 oz/sq. yard
Fiber denier: 2.2
Frazier Air Flow: 540
Membrane Bead Thickness: 4.0 mils
Surface Speed: 18 inches/min.

EXAMPLE VII

Reinforcing web: Lutravil Sales Co. LUTRASIL 5020
Type: Polypropylene spunbonded and thermally point bonded non-woven
Nominal web thickness: 6.5 mils
Sheet weight: 0.59 oz/sq.yd.
Fiber denier: 1.75
Frazier Air Flow: 981
Membrane bead thickness: 7.0 mils wet
Surface speed: 12 inches/min.

EXAMPLE VIII

Reinforcing web: Lutravil Sales Co. LUTRASIL 5015
Type: Polypropylene spunbonded and thermally point bonded non-woven
Nominal Web Thickness: 4.8 mils
Sheet weight 0.44 oz/sq.yd.
Fiber denier 1.75
Frazier Air Flow 912
Membrane bead thickness: 5.5 mils
Surface speed: 15 inches/min.

EXAMPLE IX

Reinforcing web: Eaton Dikeman Co. HOLLYTEX 6001
Type: Polypropylene spunbonded, thermally point bonded and calendered non-woven
Nominal Web Thickness: 2.5 mils
Sheet weight 0.88 oz/sq.yd.
Fiber denier 1.75
Frazier air flow 205
Membrane Bead Thickness: 5.5 mils
Surface speed: 12 inches/min.

TABLE IV

| | | IMPREGNATED WEB PERFORMANCE DATA | | | | | | | |
|---|---|---|---|---|---|---|---|---|---|
| | | Single Layer Microporous Membrane (Control)* | | | | Impregnated Web (Single Dry Layer) | | | |
| Example | Web Type | IBP (psi) | FAOP (psi) | Thickness (mils) | Flow Rate (cc/min) | IBP (psi) | FAOP (psi) | Thickness (mils) | Flow Rate (cc/min) |
| IV | REEMAY 2250 | 13.7 | 19.3 | 3.78 | 677 | 13 | 16.2 | 5.13 | 843 |
| V | HOLLYTEX 3257 | 13 | 16.2 | 5.9 | 717 | 11.8 | 13.8 | 5.13 | 803 |
| VI | HOLLYTEX 3251 | 20.3 | 21.7 | 5.37 | 482 | 19.3 | 20.3 | 4.7 | 484 |
| VII | LUTRASIL 5020 | 16.7 | 20.3 | 4.5 | 517 | 15.5 | 18 | 9.0 | 448 |
| VIII | LUTRASIL 5015 | 12.7 | 17.7 | 4.63 | 517 | 13.7 | 17.5 | 7.9 | 513 |
| IX | HOLLYTEX 6001 | 12.7 | 17.7 | 4.63 | 517 | 14 | 17.8 | 6.23 | 292 |

*Casting solution of Example III, i.e. nominal pore size of .65 microns

EXAMPLES X TO XV

Reinforced Laminated Filtration Membrane

Representative reinforced laminated filtration membranes of the present invention were made by laminating the impregnated web of Examples IV to IX to outer microporous membranes of 0.2 micron rating, such as the material described in Example I. In each case, a first outer microporous membrane was brought into contact with the impregnated web in such a manner as to provide a soaking wet contact line at the union of the two layers. A second outer microporous membrane was laid onto the opposite surface of the impregnated web in a similar manner, using appropriate spreader rollers and idler rollers. Both the impregnated web and the two outer microporous membrane layers remained wet from the cast-quench-rinse process, and had not taken any manner of thermal set before such lamination. The triple-layer laminated membrane then proceeded into the drying zone, which was a teflon coated steel drum equipped with edge restraining belts on both sides of the laminated membrane and infrared radient heaters spaced at intervals over the drum circumference. The laminate was laid onto the drum surface and under the restraining belts which are arranged to cover approximately 200° of arc over the three foot diameter drum. This arrangement allowed the laminate to dry and bond between layers under two dimensional restraining conditions, i.e., restricted stretching and contraction motion in the machine direction by sheet tension control and restricted contraction control in the web cross direction by sheet edge restraint. The bank of infrared heaters (5 heaters, 15 inches effective width, 650 Watts per unit) was run at maximum power with the parabolic mirrored heating elements spaced approximately two inches from the web and drum, and a spacing of at least seven inches between each element and its neighboring element. Drum surface speed was varied between 10 and 18 inches per minute as required to bring the material to as near to 0% moisture as such an arrangement would allow. This laminate was rolled up in a "bone dry" condition. This condition was evidenced by the heavy static charge generated as the material peeled off the drum at a point past the infrared heater banks and past the release point of the edge restraining belts. This material was wound onto a hollow core for storage, and sampled for membrane performance characteristics listed in Table V. Also listed in Table V, for comparative purposes, is the performance characteristics of the two outer layers laminated together without reinforcement. This material was then treated with cationic charge modifier pursuant to Ostreicher et al or Barnes et al with no significant changes from the performance data indicated in Table V.

EXAMPLES XVI TO XIX

Reinforced Laminated Filtration Membrane

Representative reinforced laminated filtration membranes of the present invention were made by laminating the impregnated web of Examples IV, VII, VIII and IX to outer microporous membrane roll stock of 0.45 micron rating, such as the material detailed in Example II. Laminations and drying procedures followed the method of Examples X to XV. The reinforced laminated membrane performance data is listed in Table VI, as well as the double layer non-reinforced outer layer control data.

TABLE VI

| | | REINFORCED LAMINATED FILTRATION MEMBRANE 0.2 MICRON RATED | | | | | | | |
|---|---|---|---|---|---|---|---|---|---|
| | | Double Outside Membrane Laminate (non-reinforced) | | | | Reinforced Laminate | | | |
| Example | Web Type | IBP (psi) | FAOP (psi) | Thickness (mils) | Flow Rate (cc/min) | IBP (psi) | FAOP (psi) | Thickness (mils) | Flow Rate (cc/min) |
| XVI | REEMAY 2250 | 28.1 | — | 5.86 | 221 | 28.7 | 32 | 10.6 | 182 |
| XVII | LUTRASIL 5020 | 32.3 | — | 5.6 | 180 | 32.2 | 36.8 | 13.2 | 132 |
| XVIII | LUTRASIL 5015 | 29.7 | 34 | 5.83 | 170 | 34 | 38 | 12.3 | 116 |
| XIX | HOLLYTEX 6001 | 29.7 | 34 | 5.83 | 170 | 35.3 | 39.3 | 11.5 | 101 |

EXAMPLE XX

Comparative Example

A casting solution containing 13 wt. % solids (of nylon) was prepared by the method of Example I to produce a membrane having a substantially higher than normal IBP with the expectation that the casting solution would display a decreased membrane IBP when cast into a reinforcing web.

It has been noted that in preparing impregnated webs of pore sizes less than 0.65 micron and with greater than, say, 20 psi Initial Bubble Point, a bubble point depression is noticed between the membrane alone and the impregnated web. That is, the IBP of an impregnated web is consistently lower than the IBP of a non-reinforced membrane cast from the same casting solution when the casting solution is of such character as to produce 0.2 and 0.45 micron membranes. This phenomena is not noticed with 0.65 micron membrane-producing casting solutions. It is necessary, then, to formulate a casting solution with a substantially higher IBP characteristic than 45 psi in order to obtain 0.2 micron rated impregnated webs. Although not extensively studied, we have been able to predict bubble point depressions for given impregnated web.

The casting solution was then cast as a membrane in the same fashion as Example I to obtain control data, which is noted in the Table VII.

Impregnated webs having a nominal pore size rating of 0.2 microns was prepared from this casting solution

TABLE V

| | | REINFORCED LAMINATED FILTRATION MEMBRANE 0.2 MICRON RATED | | | | | | | |
|---|---|---|---|---|---|---|---|---|---|
| | | Double Outside Membrane Laminate (non-reinforced) | | | | Reinforced Laminate | | | |
| Example | Web Type | IBP (psi) | FAOP (psi) | Thickness (mils) | Flow Rate (cc/min) | IBP (psi) | FAOP (psi) | Thickness (mils) | Flow Rate (cc/min) |
| X | REEMAY 2250 | 45.2 | — | 5.09 | 91.9 | 45 | 54 | 10.6 | 91.7 |
| XI | HOLLYTEX 3257 | 46.4 | — | 4.57 | 85.2 | 48.7 | 54.8 | 9.65 | 96.3 |
| XII | HOLLYTEX 3251 | 47.7 | 54.4 | 4.7 | 82.6 | 50.2 | 57 | 8.9 | 70 |
| XIII | LUTRASIL 5020 | 43.3 | — | 5.28 | 103 | 40.3 | 45.3 | 13.4 | 98.3 |
| XIV | LUTRASIL 5015 | 42.3 | 51.5 | 5.38 | 81.3 | 47.5 | 56.7 | 11.6 | 85 |
| XV | HOLLYTEX 6001 | 42.3 | 51.5 | 5.38 | 81.3 | 50.3 | 60.9 | 10.9 | 57.3 |

Table V indicates that the reinforced laminate of this invention has substantially the same flow as a non-reinforced double laminate having the same outer membranes.

by the methods and apparatus of the present invention. The reinforced web was a calendered non-woven polyester spunbonded scrim, Eaton Dikemann Corp.'s product HOLLYTEX 3257, having a nominal sheet thickness of 3.0 mils, sheet weight of 1.00 oz/sq. yd., fiber denier of 2.2 and Frazier air flow of 300. The web was slit to 12¾" width on a 600 ft. roll and mounted over the casting apparatus of FIG. 1. The braking force on the feed was sufficient to provide a sheet back-tension of 2.0 lbs. across the web.

In the present Example, the aforementioned Procedures for Preliminary Settings and Start-Up were followed. The only adjustments made to the settings in the course of the run were to decrease the speed from 30 inches/min to 24 inches/min when the bead thickness was increased from 5.7 to 6.8 mils wet.

The data in Table VIII was obtained when the casting solution described in Table VII was used to impregnate the HOLLYTEX 3257 web. The resulting impregnated web was dried in a restrained condition in a single layer. Double layered material is shown in Table IX. For comparative purposes the dry double layer Pall pharmaceutical cartridge's polyester reinforced 0.2 micron nylon membrane data is included in Table VIII and IX.

TABLE VII

CONTROL DATA

| Casting Solution Composition | |
|---|---|
| Nylon | 13 wt. % |
| Formic Acid | 78.70 wt. % |
| Methanol | 8.30 wt. % |

| Casting Solution Mixing Conditions | |
|---|---|
| Temperature | 30° C. |
| Time-hrs. | 3 |
| Pressure | 0.0 psig |

| Membrane Characteristics | IBP (psi) | FAOP (psi) | THICK (mils) | Q (cc/min.) |
|---|---|---|---|---|
| Dry single layer | 61.3 | 76.7 | 3.07 | 41.3 |
| Dry-laminated double layer | 72 | 85.7 | 5.63 | 18.3 |

TABLE VIII

Impregnated Web Single Layer

| Impregnated Web | Wet Membrane Bead Thickness (mils) | Dry Single Layer Characteristics | | | |
|---|---|---|---|---|---|
| | | IBP (psi) | FAOP (psi) | Thickness (mils) | Q (cc/min) |
| A | 4.5 | 28.3 | 44 | 4.07 | 81.7 |
| B | 5.7 | 34.7 | 52.3 | 4.47 | 79.7 |
| C | 6.8 | 31.7 | 63.3 | 4.7 | 63.6 |
| D | 8.0 | 43.7 | 72 | 5.15 | 44.7 |

When the same impregnated webs (A–D) were dry-laminated as double layers, the following data was obtained:

TABLE IX

Impregnated Web Double Layer

| Impregnated Web | Dry Double Layer Characteristics | | | |
|---|---|---|---|---|
| | IBP (psi) | FAOP (psi) | Thickness (mils) | Q (cc/min.) |
| A | 43.3 | 55.7 | 7.72 | 47.3 |
| B | 44.3 | 62.7 | 8.4 | 40 |
| C | 52.7 | 66.7 | 9.43 | 34 |
| D | 57.7 | 72 | 9.4 | 29.7 |
| Pall Corp. double layer reinforced | 48.8 | 53.1 | 11.63 | 35.8 |

TABLE X

Nonreinforced Double Layer

| Sample | IBP (psi) | FAOP (psi) | Thickness (mils) | Q (cc/min.) |
|---|---|---|---|---|
| AMF Cuno ZETAPOR Double-layer Membrane nonreinforced | 45.2 | — | 5.09 | 91.9 |
| Pall Double Layer Membrane, non-reinforced | 45.9 | 55.1 | 5.32 | 94.7 |

Of particular importance to this invention is the comparatively low flow rates of the traditional type of 0.2 micron rated polyester-reinforced nylon membrane exemplified by the Pall Double Layer reinforced material and the present invention's double layer reinforced material as typified in Table IX. For a given Initial Bubble Point that would be considered a sterilizing grade, i.e. 45 psi, flow rates of non-reinforced nylon membranes are more than double the flow rates of these reinforced materials.

Additionally, when comparing, for example, a 0.2 micron rated, laminated filtration membrane of this invention (exemplified by Examples X–XV) with the foregoing comparative data (Table VII–X) one can see that for substantially the same micron rating, i.e. IBP, the filtration membrane of this invention (a) permits flow rates greater than that of a single layer of impregnated reinforcing web, (b) permits flow rates substantially greater than double layered impregnated reinforcing web and (c) permits flow rates about equivalent to double layered non-reinforced membrance.

What is claimed is:

1. A process for producing an integral single layer polymeric microporous filter membrane within which a reinforcing web is embedded, comprising:
    (a) preparing a first and second reservoir of a casting solution of a polymer in a solvent system comprising a mixture of at least one solvent and one non-solvent for the polymer, the amount of non-solvent being no greater than an amount required to induce nucleation of the solution to obtain a visible precipitate;
    (b) passing a reinforcing web through the first reservoir, completely surrounding the web with casting solution and depositing a sufficient amount of the solution onto the web to completely coat the web;
    (c) directly passing the coated web from step (b) through a calendering means to simultaneously calender both sides of the coated web under conditions sufficient to provide for the penetration of the solution into the web and to remove substantially all entrapped air from the web; and
    (d) passing the calendered reinforcing web from step (c) through the second reservoir, completely surrounding the web with casting solution and depositing a sufficient amount of the solution onto the web to again completely coat the web; and
    (e) passing the coated web from step (d) through a quenching bath comprising a non-solvent system for the polymer for a time sufficient to form micropores throughout the coatings to thereby form a single layer microporous filter membrane within which a reinforcing web is embedded.

2. The process of claim 1 wherein:
    (i) the polymer is nylon;
    (ii) the solvent is formic acid;

(iii) the non-solvent is selected from the group consisting of methanol, methyl formate, water and glycerol; and (iv) the non-solvent system is a mixture of methanol and water or formic acid and water.

3. The process of claim 1, wherein the membrane has a pore size of at least 0.05 microns.

4. The process of claim 1, wherein the membrane is symmetrical and isotropic.

5. The process of claim 1, wherein the polymer is nylon.

6. The process of claim 1, wherein the reinforcing web is wettable by the casting solution.

7. An integral single layer polymeric microporous filter membrane within which a reinforcing web is embedded produced by the process of claims 1, 2 or 5.

* * * * *

UNITED STATES PATENT AND TRADEMARK OFFICE

Certificate

Patent No. 4,645,602                                          Patented: February 24, 1987

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is Matthew Miller, Mark T. Meyering and Todd Williams.

Signed and Sealed this Thirtieth Day of May 1989.

Jeffery V. Nase
*Supervisory Petitions Examiner*
*Office of the Deputy Assistant*
*Commissioner for Patents*